US012229960B2

(12) United States Patent
Duval et al.

(10) Patent No.: US 12,229,960 B2
(45) Date of Patent: *Feb. 18, 2025

(54) SYSTEMS AND METHODS FOR DIAGNOSING AND/OR MONITORING DISEASE

(71) Applicant: Boston Scientific Scimed, Inc., Maple Grove, MN (US)

(72) Inventors: George W. Duval, Sudbury, MA (US); John Allen Hingston, Framingham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/303,891

(22) Filed: Apr. 20, 2023

(65) Prior Publication Data

US 2023/0260124 A1 Aug. 17, 2023

Related U.S. Application Data

(63) Continuation of application No. 17/560,336, filed on Dec. 23, 2021, now Pat. No. 11,663,720, which is a
(Continued)

(51) Int. Cl.
*A61B 5/00* (2006.01)
*G06T 7/00* (2017.01)
(Continued)

(52) U.S. Cl.
CPC .......... *G06T 7/0014* (2013.01); *A61B 5/0082* (2013.01); *A61B 5/42* (2013.01);
(Continued)

(58) Field of Classification Search
CPC ......... G06T 7/0014; G06T 2207/10068; G06T 2207/30092; G06T 2207/30096;
(Continued)

(56) References Cited

U.S. PATENT DOCUMENTS 8,185,185 B2 5/2012 Gilreath et al.
2005/0124875 A1 6/2005 Kawano et al.
(Continued)

FOREIGN PATENT DOCUMENTS

CN 103687646 A 3/2014
EP 1 847 940 A2 10/2007
(Continued)

OTHER PUBLICATIONS

Ryan W. Stidham, et al., "Endoscopy and cross-sectional imaging for assessing Crohn's disease activity," Techniques in Gastrointestinal Endoscopy, 2016, pp. 123-130, vol. 18, No. 3 (8 pages).
(Continued)

*Primary Examiner* — Syed Haider
(74) *Attorney, Agent, or Firm* — Bookoff McAndrews, PLLC

(57) ABSTRACT

A method for evaluating a gastrointestinal tract may include characterizing one or more disease parameters using objective measures obtained from imaging data of a gastrointestinal tract. The one or more disease parameters reflect a measure of at least one of lesions, ulcers, bleeding, stenosis, and vasculature. The method may also include using the one or more characterized disease parameters to classify a disease state.

19 Claims, 6 Drawing Sheets

Related U.S. Application Data continuation of application No. 16/371,511, filed on Apr. 1, 2019, now Pat. No. 11,244,454.

(60) Provisional application No. 62/651,937, filed on Apr. 3, 2018.

(51) Int. Cl.

| | | |
|---|---|---|
| *G16H 10/60* | (2018.01) | |
| *G16H 20/17* | (2018.01) | |
| *G16H 30/40* | (2018.01) | |
| *G16H 40/63* | (2018.01) | |
| *G16H 50/20* | (2018.01) | |
| *G16H 50/30* | (2018.01) | |
| *G16H 50/70* | (2018.01) | |

(52) U.S. Cl.
CPC .......... *A61B 5/4216* (2013.01); *A61B 5/7264* (2013.01); *A61B 5/746* (2013.01); *G16H 10/60* (2018.01); *G16H 20/17* (2018.01); *G16H 30/40* (2018.01); *G16H 40/63* (2018.01); *G16H 50/20* (2018.01); *G16H 50/30* (2018.01); *G16H 50/70* (2018.01); *G01N 2800/065* (2013.01); *G06T 2207/10068* (2013.01); *G06T 2207/30092* (2013.01); *G06T 2207/30096* (2013.01); *G06T 2207/30101* (2013.01)

(58) Field of Classification Search
CPC .......... G06T 2207/30101; G16H 20/17; G16H 10/60; G16H 50/30; G16H 50/70; G16H 50/20; G16H 30/40; G16H 40/63; A61B 5/0082; A61B 5/42; A61B 5/4216; A61B 5/7264; A61B 5/746; G01N 2800/065
See application file for complete search history.

(56) References Cited

U.S. PATENT DOCUMENTS

| | | | |
|---|---|---|---|
| 2007/0255095 A1* | 11/2007 | Gilreath | A61B 5/4255 600/102 |
| 2008/0045811 A1 | 2/2008 | Iliff | |
| 2009/0005693 A1* | 1/2009 | Brauner | G06T 7/0012 600/481 |
| 2009/0306633 A1 | 12/2009 | Trovato et al. | |
| 2011/0159521 A1 | 6/2011 | Gong et al. | |
| 2012/0189544 A1* | 7/2012 | Shaw | A61P 35/00 424/1.73 |
| 2013/0046150 A1 | 2/2013 | Devanaboyina | |
| 2013/0225439 A1 | 8/2013 | Princen et al. | |
| 2015/0334276 A1 | 11/2015 | Ecker et al. | |
| 2017/0076448 A1 | 3/2017 | Chen et al. | |
| 2017/0249434 A1 | 8/2017 | Brunner | |
| 2018/0000358 A1 | 1/2018 | Chuang et al. | |
| 2018/0168490 A1 | 6/2018 | Jones et al. | |
| 2018/0325499 A1 | 11/2018 | Landey et al. | |
| 2019/0029504 A1* | 1/2019 | Nadiv | H04N 25/709 |
| 2019/0150760 A1* | 5/2019 | Chen | A61B 5/4848 |

FOREIGN PATENT DOCUMENTS

| | | |
|---|---|---|
| GB | 2512876 A | 10/2014 |
| JP | 2014-18332 A | 2/2014 |

OTHER PUBLICATIONS

Info CDEIS, "Crohn's disease index of severity," IG-IBD Scores: Calculators in Gastroenterology, <https://igibdscores.it/en/info-cdeis.html> (3 pages).

Info SES-CD, "Simple endoscopic score for Crohn's disease," G-IBD Scores: Calculators in Gastroenterology, <https://www.igibdscores.it/en/info-sescd.html> (3 pages).

Noa Rozendorn, et al., "A review of magnetic resonance enterography-based indices for quantification of Crohn's disease inflammation", Therapeutic Advances in Gastroenterology, 2018, pp. 1-21, vol. 11 (21 pages).

Info Mayo, Mayo Endoscopic, G-IBD Scores: Calculators in Gastroenterology, <https://www.igibdscores.it/en/info-mayo-endoscopic.html> (1 page).

* cited by examiner

SYSTEMS AND METHODS FOR DIAGNOSING AND/OR MONITORING DISEASE

CROSS-REFERENCE TO RELATED APPLICATIONS

This application is a continuation of U.S. application Ser. No. 17/560,336, filed on Dec. 23, 2021, which is a continuation of U.S. application Ser. No. 16/371,511, filed on Apr. 1, 2019, now U.S. Pat. No. 11,244,454, which claims the benefit of priority from U.S. Provisional Application No. 62/651,937, filed on Apr. 3, 2018, which are incorporated by reference herein in their entireties.

TECHNICAL FIELD

The present disclosure relates generally to devices, systems, and/or methods for diagnosing and/or monitoring disease using, for example, mucosal severity imaging. More specifically, aspects of the present disclosure pertain to devices, systems, and/or methods for quantifiably or otherwise objectively measuring disease indicators using imaging devices.

BACKGROUND

Inflammatory Bowel Disease ("IBD") is a chronic disorder characterized by chronic inflammation in the gastrointestinal ("GI") tract. The disease affects 5-6 million people worldwide, with approximately 1.6 million sufferers in the United States. Patients and health care providers may spend substantial amounts of money per year treating IBD, with annual direct costs estimated between $11-28 billion in the United States. Moreover, people with IBD may have longer and more expensive hospitalizations with higher readmission rates than people without IBD.

There are two main types of IBD: Ulcerative Colitis ("UC") and Crohn's Disease ("CD"). CD can affect any part of the digestive system and is characterized with transmural involvement. Symptoms of CD include abdominal pain, fever, cramping, rectal bleeding, and frequent diarrhea. The peak age for CD disease onset is between 15-35 years. UC affects the colon only, with mucosal involvement. UC carries mild to severe symptoms, which are similar to the symptoms of CD. With UC, complications may be less frequent than with CD. Colectomy may be used to treat UC. The peak age of disease onset for UC is between 15-30 and 50-70 years old. 55% of IBD patients have UC, and 45% of IBD patients have CD.

IBD is characterized by bouts of disease (also known as flare-ups). A correlation has been shown between inflammatory markers and gut motility disorders. For example, it has been reported that CD subjects have lower amplitudes for small bowel contractions with an increase of peristalsis frequency. Motor abnormalities have been shown to be more frequent in patients with active CD. Patients with inactive CD have also shown marked gastrointestinal motor disorders characterized by reduced incident of small bowel contractions and increased incidence of single or clustered propagated contractions. Periods of flare-ups may be interspersed with periods of remission.

Conventional treatments focus on addressing present symptoms. However, it may be more desirable to prevent disease progression in order to obtain deep remission. Despite studies to determine biomarkers of IBD, and despite discoveries regarding clinical variables, serological markers, fecal markers, and genetic tests, no single test is predictive, and no monitoring system exists. Conventional methods for diagnosing and monitoring IBD lack a robust ability to identify remission and disease states and to monitor progression of disease. For example, current indices for evaluating IBD may not be as objective as needed.

SUMMARY

Examples of the present disclosure relate to, among other things, devices, systems, and methods for diagnosing and/or monitoring disease using, for example, mucosal severity imaging. Each of the examples disclosed herein may include one or more of the features described in connection with any of the other disclosed examples.

In one example, a method for evaluating a gastrointestinal tract may include characterizing one or more disease parameters using objective measures obtained from imaging data of a gastrointestinal tract. The one or more disease parameters reflect a measure of at least one of lesions, ulcers, bleeding, stenosis, and vasculature. The method may also include using the one or more characterized disease parameters to classify a disease state.

The objective measures include at least one quantitative measure. The one or more disease parameters may reflect a measure of at least one of an ulcer or a lesion. The objective measure may include at least one of depth or size. The disease may be an irritable bowel disease. The method may further include comparing the one or more disease parameters to one or more threshold values. The method may further include aggregating at least two of the one or more characterized disease parameters. Using the one or more characterized disease parameters may include using the aggregated at least two of the one or more characterized disease parameters. The method may further include aggregating at least two of the one or more characterized disease parameters. Using the one or more characterized disease parameters may include using the aggregated at least two of the one or more characterized disease parameters. The method may further include comparing the aggregated at least two of the one or more characterized disease parameters to at least one threshold value. The one or more disease parameters may be one or more first disease parameters. The disease state may be a first disease state. The method may further include storing at least one of the one or more characterized disease parameters or the disease state. The method may further include using an objective measure obtained from additional imaging data of the gastrointestinal tract in order to characterize one or more second disease parameters. The method may further include using the one or more characterized second disease parameters to classify a second disease state. The method may further include comparing at least one of the one or more second disease parameters to at least one of the one or more first disease parameters. The method may further include comparing the second disease state to the first disease state. The method may further include, based on the classified disease state, providing at least one of an alert or a treatment. The imaging data may be data captured at more than one location in a gastrointestinal tract. The classified disease state may be at least one of an active disease state or a remission disease state. The one or more disease parameters may include parameters to reflect measures of at least two of lesions, ulcers, bleeding, stenosis, and vasculature. The one or more disease parameters may include parameters to reflect measures of at least three of lesions, ulcers, bleeding, stenosis, and vasculature.

In another example, a method for evaluating a gastrointestinal tract may include receiving data from at least one imaging device located in a lumen of a gastrointestinal tract. The method may also include, based on the data received from the at least one imaging device, characterizing a disease parameter. The disease parameter may reflect a measure of at least one of lesions, ulcers, bleeding, stenosis, and vasculature. The method may further include comparing the disease parameter to at least one threshold value.

Characterizing a disease parameter may include using a quantitative measure. The disease parameter may reflect a measure of at least one of an ulcer or a lesion. The objective measure may include at least one of depth or size. The disease parameter may be a first disease parameter. The method may further include, based on the data received from the at least one imaging device, characterizing a second disease parameter. The second disease parameter may reflect a measure of at least one of lesions, ulcers, bleeding, stenosis, and vasculature. The method may further include aggregating the first and second disease parameters. The disease parameter may be a first disease parameter. The threshold value may account for an earlier characterization of the same disease parameter. The method may further include, based on the comparison, characterizing the disease parameter as worsening, lessening, or remaining stable. The method may further include, based on a result of the comparison, providing at least one of an alert or a treatment.

In another method, a system for evaluating gastrointestinal motility may include an imaging device configured to capture image data in a gastrointestinal lumen of a patient. The device may be further configured to measure an objective measure obtained from the data in order to characterize one or more disease parameters and provide the one or more characterized disease parameters to classify a disease state.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal."

BRIEF DESCRIPTION OF THE DRAWINGS

The accompanying drawings, which are incorporated in and constitute a part of this specification, illustrate examples of the present disclosure and together with the description, serve to explain the principles of the disclosure.

DETAILED DESCRIPTION

The present disclosure is drawn to for devices, systems, and methods for diagnosing and/or monitoring irritable bowel disease using, for example, mucosal severity imaging. In particular, in at least some aspects, the systems and methods may be used to diagnose, monitor, and/or predict IBD conditions, including flare-ups, by quantifying parameters such as size and depth of lesions or ulcers, bleeding, stenosis, and vasculature. The devices, systems, and methods for diagnosis and/or monitoring using mucosal severity imaging described herein may also be used to monitor other conditions including, for example, other gastrointestinal conditions such as irritable bowel syndrome, gastritis, gastroesophageal reflux disease (GERD), Barrett's esophagus, polyps, colorectal cancer, chronic asthma, chronic bronchitis, peptic ulcer, dysphagia, cholecystitis, diverticular disease, celiac disease, and emphysema. Although IBD monitoring is referenced herein, reference to IBD should not be construed as limiting the possible applications of the disclosed systems.

Figure 1:
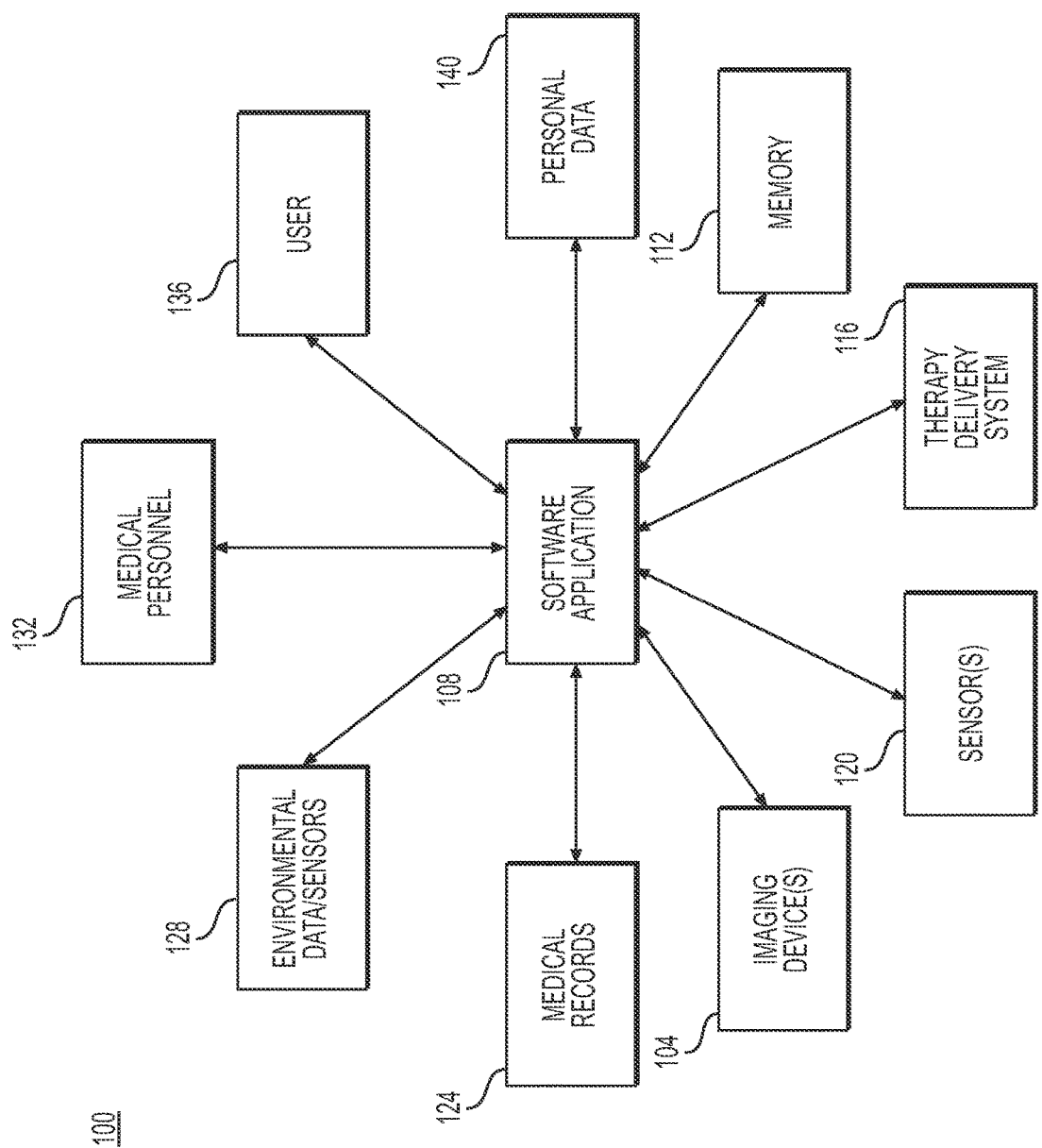
FIG. 1 depicts an exemplary mucosal severity monitoring system.

FIG. 1 depicts an exemplary mucosal severity monitoring system 100. Mucosal severity monitoring system 100 may include one or more imaging devices 104, one or more software applications 108, memory 112, one or more therapy delivery systems 116, one or more sensors 120, medical records 124, environmental data/sensors 128, medical personnel 132, and one or more users 136.

Imaging device 104 may be an imager capable of taking images including optical, infrared, thermal, or other images. Imaging device 104 may be capable of taking still images, video images, or both still and video images. Imaging device 104 may be configured to transmit images to a receiving device, either through a wired or a wireless connection. Imaging device 104 may be, for example, a component of an endoscope system, a component of a tool deployed in a working port of an endoscope, a wireless endoscopic capsule, or one or more implantable monitors or other devices. In the case of an implantable monitor, such an implantable monitor may be permanently or temporarily implanted.

Imaging device 104 may be configured to capture images at one or more locations of the GI tract, including the esophagus, stomach, duodenum, small intestine, and/or colon. For example, during an endoscopy procedure, an imaging device 104 carried on an endoscope or a tool deployed in an endoscope may be advanced through various portions of the GI tract, and images may be captured at numerous locations in a given portion or across portions. Imaging device 104, a device carrying imaging device 104, or another component of mucosal severity monitoring system 100, such as software application 108, may be capable of determining the location of the GI tract where images were recorded. For example, imaging device 104, a device carrying imaging device 104, or another component of mucosal severity monitoring system 100, such as software application 108, may be able to determine whether images were taken in the esophagus, the stomach, the ileum, the right colon, the transverse colon, the left colon, the rectum, or the jejunum. An imaging device 104 carried by a wireless endoscopic capsule may capture images at various points as it traverses the GI tract. An imaging device 104 which is part of an implantable monitor may be fixed in one location or may be capable of capturing images at multiple locations. For example, an implantable monitor may include numerous imaging devices 104 at different locations within the GI tract. Imaging device 104 may capture images continually or periodically.

Imaging device 104 may be configured to capture data relevant to actual size and depth of lesions, ulcers, and/or other abnormalities within the GI tract. Size of a lesion or ulcer may range from a scale of 100 micrometers to a few centimeters. Depth information captured may be relevant to classifying depth as being superficial, submucosal, and/or muscularis. Imaging device 104 may also be configured to capture data regarding the prevalence of impact of lesions or ulcers on a specific region of the GI tract (for example, the esophagus, stomach, ileum, right colon, transverse colon, left colon, rectum, and/or jejunum).

Imaging device 104 may further be configured to capture information regarding inflammation. For example, imaging device 104 may be capable of capturing data regarding vasculature including patchy obliteration and/or complete obliteration. Imaging device 104 may be configured to capture information regarding structure of blood vessels including dilation or over-perfusion. Imaging device 104 may also be capable of capturing data relevant to blood flow including perfusion information and real-time perfusion information. For example, imaging device 104 may be configured to capture data relevant to blood's permeation into a tissue. Imaging device 104 may also capture data relevant to tissue thickening, which may be the result of increased blood flow to a tissue and possible obliteration of blood vessels and/or inflammation.

Imaging device 104 may also be configured to measure stenosis in the GI tract. In other words, imaging device 104 may be configured to assess the amount of narrowing in various regions of the GI tract. Imaging device 104 may also be configured to assess, for example, tissue properties such as stiffness. For example, stiffness may be monitored during expansion of a balloon or stent to prevent unwanted fissures or damage. Imaging device 104 may further be configured to assess bleeding. For example, imaging device 104 may capture data relevant to spots of coagulated blood on a surface of mucosa which can implicate, for example, scarring. Imaging device 104 may also be configured to capture data regarding free liquid in a lumen of the GI tract. Such free liquid may be associated with plasma in blood. Furthermore, imaging device 104 may be configured to capture data relevant to hemorrhagic mucosa and/or obliteration of blood vessels.

An implantable device including one or more imaging devices 104 may be delivered via a natural orifice transluminal endoscopic surgery (NOTES) procedure, potentially during a colonoscopy. For example, during a colonoscopy, an incision may be made and a sensor may be implanted outside of the lumen on the omentum. Use of such a procedure may provide benefits including use of an endoscopy suite rather than an operating room. If imaging devices 104 require a battery, a battery may be changed during a routine colonoscopy. Imaging devices 104 may also be delivered via laproscopic surgery or a different surgical or non-surgical procedure.

Imaging device 104 may be in communication either directly or indirectly with a software application 108, which may be stored on a processor or other suitable hardware. Imaging device 104 may be connected with software application 108 by a wired or wireless connection. In the alternative, imaging device 104 may be in communication with another type of processing unit. Software application 108 may run on a specialized device, a general-use smart phone or other portable device, and/or a personal computer. Software application 108 may also be part of an endoscope system, endoscope tool, wireless endoscopic capsule, or implantable device which also includes imaging device 104. Software application 108 may be connected by a wired or wireless connection to memory 112, therapy delivery system 116, one or more sensors 120, medical records 124, environmental data input/sensors 128, medical personnel 132, user 136, and/or personal data 140. Software application 108 may be able to run on multiple platforms using data for the same patient. Multiple users (such as a patient, medical professional, or other caregiver) may be able to access software application 108 concurrently or otherwise.

Software application 108 or any other kind of processing unit may analyze signals from imaging device 104 and other inputs (such as sensor 120, medical records 124, environmental data input/sensors 128, medical personnel 132, user 136, and/or personal data 140) and extract information from the data obtained by imaging device 104 and the other inputs. Software application 108 or any other suitable component may apply an algorithm to the signals or data from imaging device 104 and other inputs. Software application 108 may store information regarding algorithms, imaging data, or other data in memory 112. The data from inputs such as imaging device 104 may be stored by software application 108 in memory 112 locally on a specialized device or a general-use device such as a smart phone or computer. Memory 112 may be used for short-term storage of information. For example, memory 112 may be RAM memory. Memory 112 may additionally or alternatively be used for longer-term storage of information. For example, memory 112 may be flash memory or solid state memory. In the alternative, the data from imaging device 104 may be stored remotely in memory 112 by software application 108, for example in a cloud-based computing system.

Software application 108 may interface with a source of medical records 124. Software application 108 may further communicate with a source of environmental data 128. Environmental data source 128 may include environmental data sensors. Software application 108 may facilitate the entry of data by a user via user 136 or by medical personnel 132 via a medical personnel input. Data may be entered by a user 136 and medical personnel 132 either locally or remotely. For example, data regarding symptoms such as diarrhea or cramps may be entered via a user 136 and/or a medical personnel 132. User 136 and/or medical personnel 132 may enter information regarding when therapies such as medications were administered (e.g., started or finished). The user input and the medical personnel input may constitute the same or separate components of mucosal severity monitoring system 100. Software application 108 may also communicate with personal data source 140. Medical records source 124, environmental data source 128, the input from medical personnel 132, the input from user 136, and personal data source 140 may be separate or may be integrated with one another in various combinations.

Software application 108 may be configured to analyze data captured by imaging device 104 related to, for example, inflammation, lesions and/or ulcers, stenosis, and bleeding, as described above. Software application 108 may, alone or in combination with other applications, process data from imaging device 104 to, for example, evaluate vasculature. For example, software application 108 may be configured to detect patchy and/or complete obliteration of blood vessels. Software application 108 may also be configured to assess perfusion (e.g., real-time blood flow) intensity in one or more areas of the GI tract.

Software application 108 may further be configured to process information regarding lesions, ulcers, and/or other tissue abnormalities. For example, software application 108 or another component of mucosal severity monitoring system 100 may be configured to accurately measure the size (width and/or length) of a lesion and/or ulcer and may also be configured to measure the depth of a lesion and/or ulcer. Software application 108 may be configured to classify a depth of a lesion and/or ulcer as superficial, submucosal, and/or muscularis. Software application 108 may also be configured to accurately identify and assess the impact of lesions and/or ulcers on one or more specific regions of the GI tract (e.g., the esophagus, stomach, ileum, right colon, transverse colon, left colon, rectum, and/or jejunum). For example, software application 108 may compare the relative prevalence of lesions and/or ulcers across different regions of the GI tract. For example, software application 108 may calculate the percentage of affected surface area of a GI tract and compare different regions of the GI tract. As a further example, software application 108 may quantify the number of ulcers and/or lesions in a particular area of the GI tract and compare that number with other areas of the GI tract. Software application 108 may also consider relative severity of ulcers and/or lesions in an area of the GI tract by, for example, classifying one or more ulcers and/or lesions into a particular pre-determined classification, by assigning a point scoring system to ulcers and/or lesions based on severity, or by any other suitable method. Software application 108 may also aggregate its consideration of ulcers and/or lesions across different portions of the GI tract in order to evaluate the GI tract as a whole or the health of some combination of areas in the GI tract.

Software application 108 may also be configured to assess stenosis in one or more areas of the GI tract, or in the GI tract as a whole. For example, application 108 may utilize data obtained by imaging device 104 or any other input (e.g., sensors 120) in order to assess the amount of narrowing in various regions of the GI tract. Software application 108 may further be configured to assess bleeding in the GI tract using data from, for example, imaging device 104. For example, software application 108 may be configured to detect spots of coagulated blood on surfaces of mucosa, to detect free liquid (e.g., plasma) in a lumen of the GI tract, and/or to detect hemorrhagic mucosa.

Software application 108, along with one or more imaging devices 104, may be configured to quantify severity of one or more symptoms or characteristics of a disease state. For example, software application 108 may be configured to assign quantitative or otherwise objective measure to one or more disease conditions such as ulcers/lesions, inflammation, stenosis, and/or bleeding. Software application 108 may also be configured to assign a quantitative or otherwise objective measure to a severity of a disease as a whole. Such quantitative or otherwise objective measures may, for example, be compared to one or more threshold values in order to assess the severity of a disease state. Such quantitative or otherwise objective measures may also be used to take preventative or remedial measures by, for example, administering treatment through therapy delivery system 116 as discussed below or by providing an alert (e.g., to medical personnel, a patient, or a caregiver).

Software application 108 may store the results or any component of its analyses, such as quantitative or otherwise objective measures, in memory 112. Results or information stored in memory 112 may later be utilized for, for example, tracking disease progression over time. Such results may be used to, for example, predict flare-ups and take preventative or remedial measures by, for example, administering treatment through therapy delivery system 116 as discussed below or by providing an alert (e.g., to medical personnel, a patient, or a caregiver).

In performing the types of analyses described above, software application 108 may rely on data collected by various components of mucosal severity monitoring system 100. For example, software application 108 may rely on the types of data (described above) that may be collected by imaging device 104. Software application 108 may also rely on inputs from other sources, including, for example, sensors 120, medical records 124, environmental data 128, medical personnel 132, user 136, and/or personal data 140.

Mucosal severity monitoring system 100 may also include a therapy delivery system 116. Therapy delivery system 116 may be in communication with imaging device 104, either directly or via software application 108. Therapy delivery system 116 may be a component of, for example, an implantable device or an external wearable device. Therapy delivery system 116 may be a component of any of the delivery systems including imaging device 104 or may be a component of a separate device. Therapy delivery system 116 may be used to administer drugs. Therapy delivery system 116 may also be used to administer other therapies such as neuromodulation therapy to, for example, block or stimulate nerves or other tissue, including via vagus nerve stimulation, peripheral nerve stimulation, sympathetic nerve modulation, gastric stimulation, or other tissue modulation therapies. Therapy delivery system 116 may form part of a closed loop system and may deliver therapy automatically based upon data from inputs such as imaging device 104 and/or sensor 120 without user input. In the alternative, therapy delivery system 116 may be utilized manually by a user and/or medical personnel by way of, for example, software application 108 or another manual input. A component of mucosal severity monitoring system 100 may also recommend a treatment course to a patient, medical personnel, a caregiver, and/or another party.

Sensors 120 can measure a wide variety of parameters regarding activity of the esophagus, stomach, duodenum, small intestine, and/or colon. Depending on the parameter measured, different types of sensors 120 may be used. For example, sensor 120 may be configured to measure pH via, for example, chemical pH sensors. Sensors 120 may transmit pH measurements to, for example, software application 108 on a receiver or other device. Software application 108 may utilize a pH measurement in order to identify a specific location in the GI tract. For example, a pH of 6.5-7.5 may be indicative of the mouth, a pH of 4.0-6.5 may be indicative of the upper stomach, a pH of 1.5 to 4.0 may be indicative of the lower stomach, a pH of 7.0 to 8.5 may be indicative of the duodenum, and a pH of 4-7 may be indicative of the small or large intestine.

As a further example, gastric myoelectrical activity may be measured via, for example, electrogastrography ("EGG"). Gastric motility and/or dysmotility may be measured, via, for example, accelerometers, gyroscopes, pressure sensors, impedance gastric motility (IGM) using bioimpedance, strain gauges, optical sensors, acoustical sensors/microphones, manometry, and percussive gastogram. Gut pressure and/or sounds may be measured using, for example, accelerometers and acoustic sensors/microphones. Respiration rate may be measured using, for example, accelerometers, gyroscopes, and/or transthoracic impedance. Respiration rate may be measured so that software application 108 or another component can filter out respiratory activity from the GI signals software application 108 is analyzing. Certain of sensors 120 may be used only at certain times in order to conserve battery. For example, it may be desirable to perform a higher-frequency sampling with an EGG-type sensor 120 during rest or sleep to avoid external noise and obtain a cleaner signal.

Sensors 120 may also measure other factors which may have a correlation with flare ups and may indicate quality of life. For example, accelerometers, gyroscopes, GPS sensors, temperature sensors, blood pressure sensors, and the like may be used to measure factors such as posture; activity level; and sleep/waking cycles, including the depth, duration, and number of awakenings during sleep periods. Stress levels may be measured via heart rate sensors, galvanic skin response, respiratory sinus arrhythmia (using, for examples, sensors described above for respiration), or other autonomic tone measures. Stress levels may also be entered via manual input, for example via input by medical personnel 132 or user 136.

Gastric dysrhythmia may be measured with the types of measurements described above for gastric myoelectrical activity and gastric motility/dysmotility. Sensors 120 may also measure electro-mechanical uncoupling, which is where electrical activity is present but contractile activity is lacking. Sensors 120 may include acoustic, pressure, and/or other types of sensors to identify the presence of high electrical activity but low muscle response indicative of electro-mechanical uncoupling. When electro-mechanical uncoupling occurs, sensors 120, alone or in combination with the other components of mucosal severity monitoring system 100, may measure propagation of slow waves in regions such as the stomach, intestine, and colon. Software application 108 or another component of mucosal severity monitoring system 100 may classify any dysrhythmia as bradygastria (decreased activity), tachygastria (increased activity), or arrhythmia (irregular activity) for each region, such as the stomach, intestine, and/or colon.

Imaging device 104, sensors 120, medical records source 124, environmental data source 128, input from medical personnel 132, input from user 136, and/or personal data source 140 may be used to record information in software application 108 regarding pain or discomfort levels; time of day/week/month/year; dietary intake; and environmental factors such as light, temperature, and altitude. Sensors 120, medical records source 124, environmental data source 128, input from medical personnel 132, input from user 136, and/or personal data source 140 may also be used to input demographic or other external data into software application 108. Such external data may include medical data such as prior relapse or flare-up information, medication (e.g., NSAIDs, antibiotics, hormone replacement therapy, oral contraceptives, cyclooxygenase-2, prednisone), surgeries (e.g. appendectomy or colectomy), comorbidities, and mental health information. Relevant external data may also include test data such as: gut microbiota, genomics, serological antibody markers, serological inflammatory markers (C-reactive protein, erythrocyte sedimentation rate (ESR), Interleukin (IL)-1 Beta, IL-2, IL-6, IL-8, IL-10, IL-16, IL-2 soluble receptor, tumor necrosis factor-alpha (TNF-alpha), TNF-alpha soluble receptor, IFN-gamma), white blood cell count, intestinal permeability, endoscopy results (mucosal healing, confocal laser endomicroscopy, magnifying colonoscopy, etc.), histology results, and fecal markers (e.g., fecal calprotectin, lactoferrin, S100A12, Indium 111-labeled leukocytes, alpha1-antitrypsin, alpha2-macroglobulin, myeloperoxidase, PMNelastase). Relevant external data may further include personal data such as socioeconomic status, major life events, social media feeds, and internet searches.

Based on the data and information from imaging device 104, sensors 120, medical records source 124, environmental data source 128, medical personnel 132, user 136, and/or personal data source 140, software application 108 may perform numerous analyses and generate various plots or other data. For example, software application 108 may analyze data including the quantitative and or otherwise objective measures discussed above for lesions and/or ulcers, inflammation, stenosis, and/or bleeding.

Software application 108 may generate a notification if analysis of data from imaging device 104 signals an upcoming disease flare-up or a flare-up in progress. Software application 108 may consider information from medical records source 124, environmental data source 128, medical personnel 132, user 136, and personal data source 140 when determining whether to deliver a notification. A predictive notification may be potentially generated by software application 108 up to days in advance of a flare-up. Notifications generated by software application 108 may be provided to a patient, a caregiver, and/or medical personnel. Information gathered by the software application 108 may be used to classify patients based on risk of flare-up in order to aid with predictive abilities. Software application 108 may also communicate with therapy delivery system 116 and may deliver therapy automatically based upon analysis of data from sensors 120 without user input. In the alternative, therapy delivery system 116 may be utilized manually by a user and/or medical personnel, e.g., after receiving an alert.

As shown in FIGS. 2-6, a system such as mucosal severity monitoring system 100 as depicted in FIG. 1 may apply a variety of algorithms to data collected from imaging device 104, sensors 120, medical records source 124, environmental data source 128, medical personnel 132, user 136, and/or personal data source 140. In particular, software application 108 may apply the algorithms. The algorithms may be aided by machine learning. For example, data gathered from any of the sources above may be used to train an algorithm to predict exacerbations or flare-ups. Information input regarding mediation may be used to, for example, predict or otherwise consider a patient's response to medication and enable a health care provider, patient, caregiver or other party to tailor medication treatments. Data from different sources described above may be combined in various permutations in order to enable predictive diagnostics and/or treatment recommendations. While mucosal severity monitoring system 100 is used as an exemplary system, it will be appreciated that the processes depicted in FIGS. 2-6 may be applied to data from other systems. System 100 as described with regard to FIG. 1 and any or all of the methods described with regard to FIGS. 2-6 may enable notifying a patient, health care provider, caretaker, or other party of worsening symptoms in order to provide a window of time in which to administer therapy and potentially prevent hospitalizations. For example, the examples described above and herein may enable a response to a rapid onset of symptoms. System 100 as described with regard to FIG. 1 and any or all of the methods described with regard to FIGS. 2-6 may also be able to detect exacerbations of a disease in order to alert appropriate medical personnel of the onset of an exacerbation so that a patient may obtain appropriate medical care. A disease classification and/or notification may be based on an early or a late stage of worsening symptoms and/or slow or rapid onset.

Figure 2:
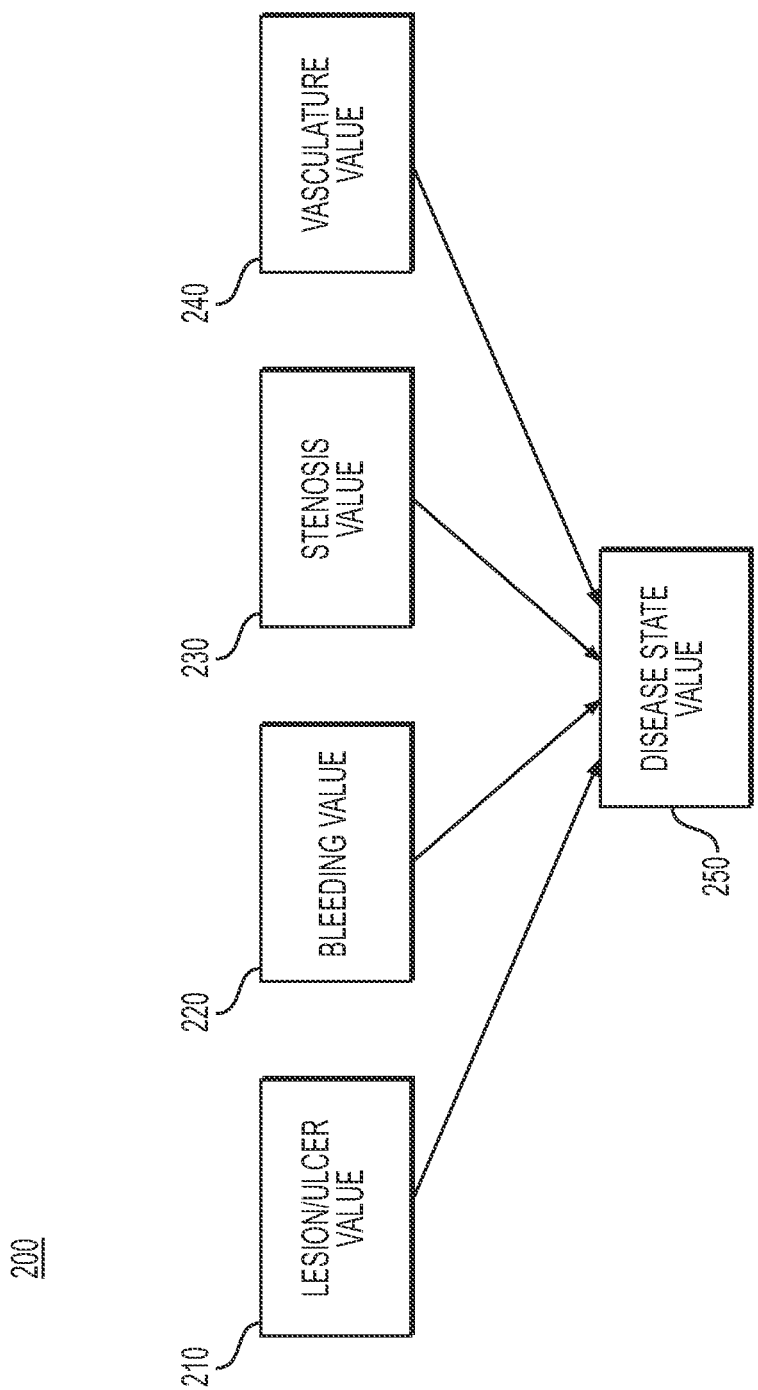
FIGS. 2-6 depict exemplary methods for evaluating a disease.

FIG. 2 shows an exemplary method 200 for evaluating various disease state parameters. For example, mucosal severity monitoring system 100 may calculate one or more of a lesion and/or ulcer value 210, a bleeding value 220, a stenosis value 230, and/or a vasculature value 240. Each of the above values may be a quantitative or otherwise objective measure and may be calculated by, for example, software application 108 and stored in memory 112. The above values may be based on data collected from imaging device 104. The above values may also be based on data from any other component of mucosal severity monitoring system 100 as described with regard to FIG. 1.

One or more of lesion and/or ulcer value 210, bleeding value 220, stenosis value 230, and/or vasculature value 240 may be combined together to result in a disease state value 250. In the alternative, disease state value 250 may be the same as lesion and/or ulcer value 210, bleeding value 220, stenosis value 230, and/or vasculature value 240. The disease state value 250 may be generated by any suitable calculation. For example, lesion and/or ulcer value 210, bleeding value 220, stenosis value 230, and/or vasculature value 240 may be added, multiplied, or otherwise combined together to provide disease state value 250. A hybrid calculation method may also be used. For example, one or more of lesion and/or ulcer value 210, bleeding value 220, stenosis value 230, and/or vasculature value 240 may be provided with a weighting value which may be applied prior to combining the values. For example, one value may be more heavily weighted than other values in calculating a disease state value. Such weighting values may be identical across patients or may vary across the patient population or be individualized. Such weighting values may be static or may change over time, by either manual input, machine learning, or any suitable method. While the illustration of method 200 contemplates assigning values to ulcers and/or lesions, bleeding, stenosis, and vasculature, method 200 can account for fewer than all of these parameters. For example, method 200 may only consider one of the parameters above or may consider a subset of these parameters.

Figure 3:
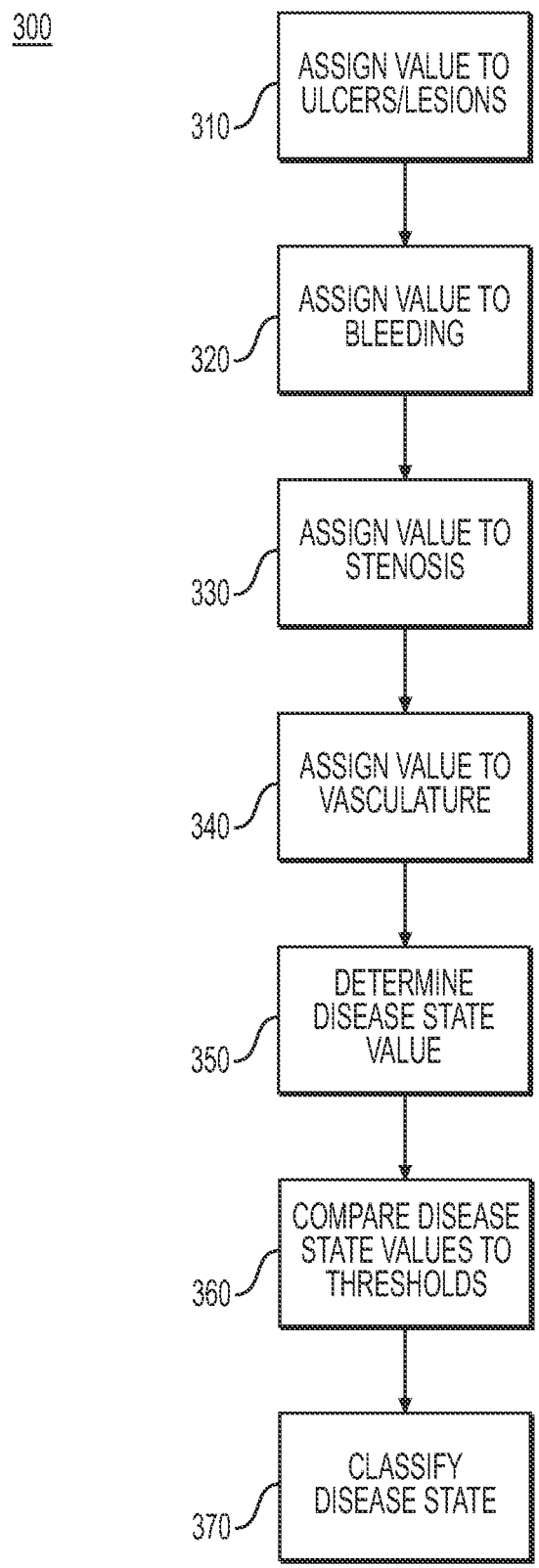

FIG. 3 shows an exemplary method 300 for classifying a disease state. Method 300 may be used in addition or in the alternative to method 200. In step 310, a component of mucosal severity monitoring system 100 such as software application 108 may assign a value to ulcers, lesions, and/or any other tissue abnormality. Such a value may be a quantitative or otherwise objective measure of ulcers and/or lesions and may measure any of the qualities of ulcers and/or lesions discussed above with regard to FIGS. 1 and 2. In step 320, a component of mucosal severity monitoring system 100 such as software application 108 may assign a value to bleeding. Such a value may be a quantitative or otherwise objective measure of bleeding and may measure any of the qualities of bleeding discussed above with regard to FIGS. 1 and 2. In step 330, a component of mucosal severity monitoring system 100 such as software application 108 may assign a value to stenosis. Such a value may be a quantitative or otherwise objective measure of stenosis and may measure any of the qualities of stenosis discussed above with regard to FIGS. 1 and 2. In step 340, a component of mucosal severity monitoring system 100 such as software application 108 may assign a value to vasculature. Such a value may be a quantitative or otherwise objective measure of vasculature and may measure any of the qualities of vasculature discussed above with regard to FIGS. 1 and 2.

In step 350, a component of mucosal severity monitoring system 100 such as software application 108 may determine a disease state value. A disease state value determined in step 350 may be the same as the disease state value 250 described above with regard to FIG. 2. The disease state value calculated in step 350 may account for all or any subset of the ulcer and/or lesion value calculated in step 310, the bleeding value calculated in step 320, the stenosis value calculated in step 330, and/or the vasculature value described in step 340. The disease state value may be equal to one of the ulcer and/or lesion value calculated in step 310, the bleeding value calculated in step 320, the stenosis value calculated in step 330, and/or the vasculature value described in step 340, or to any combination of those values.

In step 360, a component of mucosal severity monitoring system 100 such as software application 108 may compare a disease state value calculated in step 350 to one or more threshold values. For example, each value calculated in steps 310, 320, 330, 340, and 350 may be compared to a different threshold value. In the alternative, the values calculated in those steps may be aggregated in different manners before being compared to one or more threshold values. The threshold values considered in step 350 may be indicative of boundaries for certain disease states. For example, the thresholds may define varying degrees of disease severity. The thresholds may also be indicative of, for example, a flare-up or other active disease state or a remission.

In step 370, the disease state may be classified by, for example, a disease's severity, its status (e.g., active or in remission), or any other relevant disease characteristic. The comparisons of values with the same or different thresholds may produce different results. For example, one threshold comparison may be indicative of, for example, an active disease state, while another threshold comparison may be indicative of, for example, remission. One threshold comparison may be weighted more heavily than another in such a circumstance. For example, one of ulcers and/or lesions, bleeding, stenosis, and/or vasculature may be weighted more heavily than the other indicators. In addition or in the alternative, if a certain number of threshold comparisons are indicative of, for example, an active disease state or flare-up, the disease state may be classified as an active disease state or as a flare-up. For example, only one indicator (either a value or a threshold comparison) of active disease or flare-up may be necessary to classify a disease state as an active disease state or a flare-up. In the alternative, a certain number of indicators (either a value or a threshold comparison) of active disease or flare-up may be necessary to classify a disease state as an active disease state or a flare-up. The magnitude of any one value and/or threshold comparison may also be considered. For example, one or more indicators (e.g., ulcers and/or lesions, bleeding, stenosis, and/or vasculature) may be severe enough to classify a disease state independently or with less weight from the other indicators.

The disease state classification in step 370 may also account for comparisons with previous disease states, which may be stored in memory 112. For example, a disease state may be classified as more or less serious than a previously assessed disease state. Therefore, disease progression may be tracked quantitatively or using other objective measures.

While the steps illustrated in method 300 contemplate assigning values to ulcers and/or lesions, bleeding, stenosis, and vasculature, method 300 can account for fewer than all of these parameters. For example, method 300 may only consider one of the parameters above or may consider a subset of these parameters.

Figure 4:
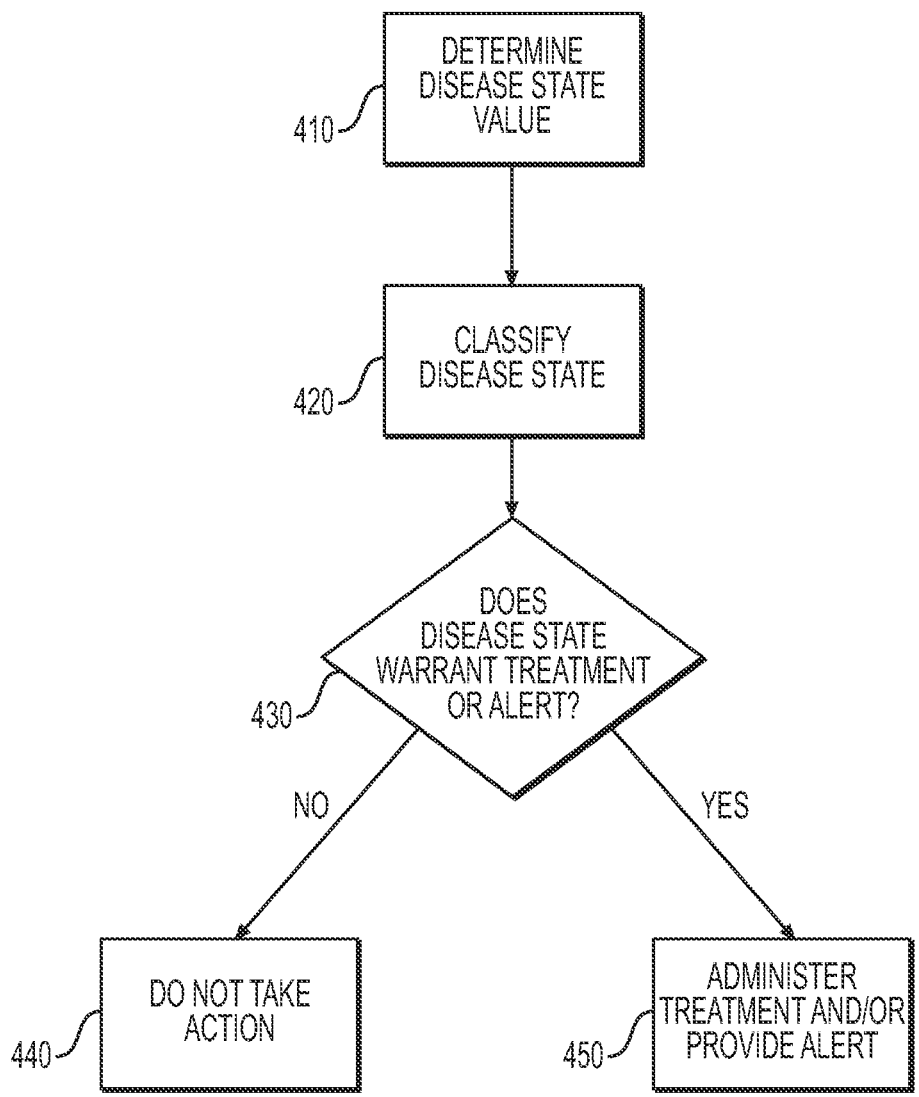

FIG. 4 shows an exemplary method 400 for classifying a disease state and administering treatment and/or providing an alert. Any of the steps in method 400 may involve quantitative or otherwise objective measures of one or more characteristics. In step 410, a component of mucosal severity monitoring system 100 such as software application 108 may determine a disease state value. Step 410 may be the same as or similar to step 350 as described with regard to FIG. 3 and may incorporate the same factors and considerations as step 350. In step 420, a component of mucosal severity monitoring system 100 such as software application 108 may classify a disease state. Step 420 may be the same as or similar to step 370 as described with regard to FIG. 3. Step 420 and/or step 410 may also involve comparing one or more disease state values to thresholds, as described above with regard to step 360.

In step 430, a component of mucosal severity monitoring system 100 such as software application 108 may determine whether a disease state warrants treatment and/or an alert.

Step 430 may include two separate steps-one for considering whether treatment is warranted and one for considering whether an alert is warranted. In the alternative, both an alert and treatment may be considered in the same step. For example, the various indicators and values calculated in steps 310, 320, 330, 340, 350, 360, and/or 370 as described with regard to FIG. 3 may be considered in determining whether treatment and/or an alert is warranted. Step 430 may involve comparing one or more indicators or values described above with one or more threshold values. For instance, values or indicators above or below a certain threshold value may be correlated with determining whether treatment is needed. Values or indicators above or below another value may be correlated with determining whether treatment is needed. In the alternative, the threshold values for treatment and alert may be the same threshold value.

In step 440, if a disease state does not warrant treatment and/or an alert, then no alert may be provided and no treatment may be administered. However, information about such an event may be stored in, for example, memory 112 for later consideration or comparison with earlier or later measurements. In step 450, if a disease state warrants treatment and/or an alert, in step 450 such an alert may be provided and/or such a treatment may be administered. Any alert or treatment as described above may be provided or administered. A treatment may be administered by, for example, therapy delivery system 116. An alert may be made to, for example, a user, medical personnel, and/or a caretaker. Such an alert may be made through, for example, a user interface of a mobile application, desktop application, and/or other application.

Figure 5:
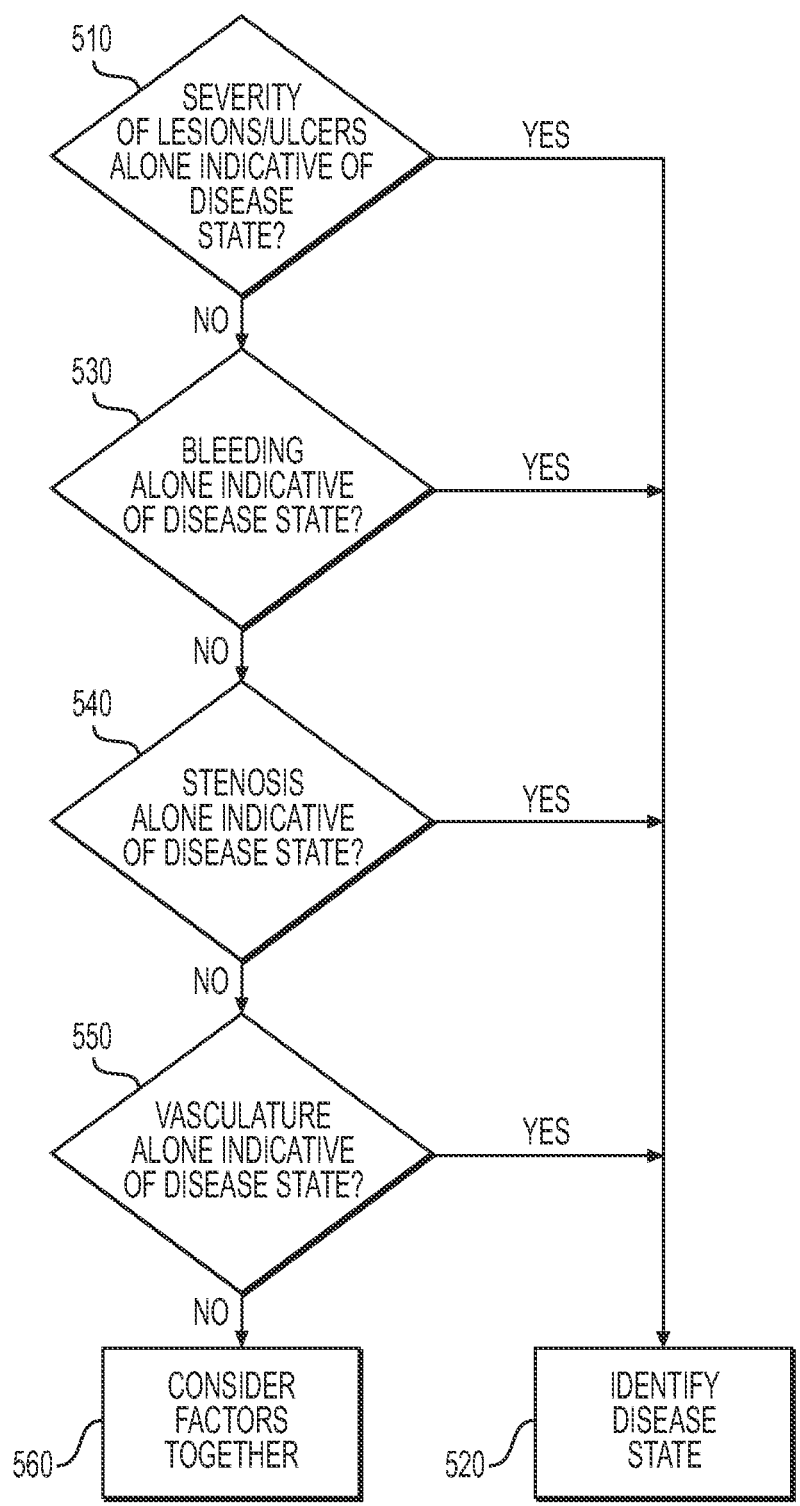

FIG. 5 depicts an exemplary process 500 for evaluating a disease state. In step 510, a component of mucosal severity monitoring system 100 such as software application 108 may evaluate whether the severity of lesions and/or ulcers alone is indicative of a disease state. For example, an absence of lesions and/or ulcers may be indicative of remission without needing to consider other factors. As a further example, the number, size, and/or depth of lesions and/or ulcers may be sufficiently large so as to indicate an active disease state or flare up. For example, step 510 may consider a lesion and/or ulcer value 210 as described with regard to FIG. 2 and/or a value assigned in step 310 as described with regard to FIG. 3. If the severity of lesions and/or ulcers is sufficient to identify a disease state, then a disease state may be identified in step 520. On the other hand, if the severity of lesions and/or ulcers alone is not indicative of a disease state, then bleeding may be considered in step 530.

In step 530, a component of mucosal severity monitoring system 100 such as software application 108 may evaluate whether bleeding alone is indicative of a disease state. Any of the indicators of bleeding discussed above (e.g., coagulated blood, free liquid, hemorrhagic mucosa, and/or obliteration of blood vessels) may be considered in step 530. For example, step 530 may consider a bleeding value 220 as described with regard to FIG. 2 and/or a bleeding value assigned in step 320 as described with regard to FIG. 3. If measurements regarding bleeding alone are sufficient to identify a disease state, then in step 520, a disease state may be identified. If measurements regarding bleeding are insufficient to identify a disease state, then stenosis may be considered in step 540.

In step 540, a component of mucosal severity monitoring system 100 such as software application 108 may evaluate whether stenosis alone is indicative of a disease state. Any of the indicators of stenosis discussed above (e.g., number and degree of narrowings) may be considered in step 540. For example, step 540 may consider a stenosis value 230 as described with regard to FIG. 2 and/or a stenosis value assigned in step 330 as described with regard to FIG. 3. If measurements regarding vasculature alone are sufficient to identify a disease state, then in vasculature are insufficient to identify a disease state, then vasculature may be considered in step 550.

In step 550, a component of mucosal severity monitoring system 100 such as software application 108 may evaluate whether vasculature alone is indicative of a disease state. Any of the indicators of vasculature discussed above (e.g., patchy and/or complete obliteration, blood vessel structure, real-time perfusion information, and/or tissue thickening) may be considered in step 550. For example, step 550 may consider a vasculature value 240 as described with regard to FIG. 2 and/or a vasculature value assigned in step 340 as described with regard to FIG. 3. If measurements regarding stenosis alone are sufficient to identify a disease state, then in step 520, a disease state may be identified. If measurements regarding stenosis are insufficient to identify a disease state, then two or more factors may be considered together in step 560.

In step 560, a component of mucosal severity monitoring system 100 such as software application 108 may consider together all of the factors described above or any subset of the factors described above. For example, the steps of method 400 may be followed in step 560. As a further example, steps 350, 360, and 370 as described with regard to FIG. 3 may be completed in step 560. As a further example, the factors considered together may be the same as or similar to disease state value 250 as described with regard to FIG. 2.

While FIG. 5 shows an exemplary order of consideration for various parameters, the various parameters may be considered in any order. In the alternative, the parameters above or other parameters may be considered concurrently. Furthermore, while the parameters above are described as exemplary, other factors may also be considered in addition or in the alternative. Data from any of the above steps may be stored in memory 112.

Figure 6:
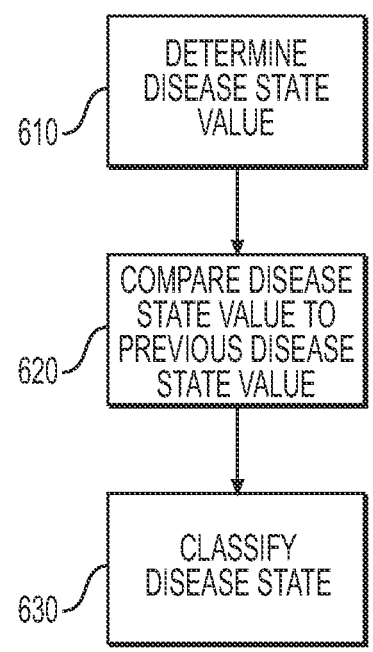

FIG. 6 shows an exemplary method 600 for classifying a disease state. In step 610, a component of mucosal severity monitoring system 100 such as software application 108 may determine a disease state value. Step 610 may be the same as or similar to any or all of the steps in exemplary method 500 as described with regard to FIG. 5, may be the same as or similar to step 410 as described with regard to FIG. 4, and/or may be the same as or similar to any of the steps in exemplary method 300 as described with regard to FIG. 3. The value determined in step 610 may be any of the values considered in method 200 described with regard to FIG. 2. For example, the value determined in step 610 may be the same as or similar to disease state value 250.

In step 620, a disease state value determined in step 610 may be compared to a previous disease state value. A previous disease state value considered in step 620 may have any or all of the characteristics of a disease state value considered in step 610 but may have been determined at a previous time. For example, a previous disease state considered in step 620 may have been stored in memory 112. The comparison in step 620 may consider more than one previous disease state value. In step 630, a disease state may be classified. For example, in step 630, a disease state may be classified with reference to a previous disease state. For example, a previous disease state may be used to establish an individualized baseline for a particular patient. Baseline values may be changed over time manually, by machine learning, or by any other suitable method. A disease state may also be classified as worsening, improving, or remaining stable. Classifying a disease state in step 630 may also include classifying a disease state trend over time. A classification may depend on the rate of change in a disease state. For example, a rapidly developing disease state may be classified in a different manner than a slowly-developing disease state. Step 630 may be the same as or similar to step 420 as described with regard to FIG. 4.

Any of the systems or methods described above may also be used to aggregate patient data. The systems or methods described above may compare information gathered from a particular patient to data collected from other patients and/or data manually input regarding patient classifications. For example, any of the systems or methods described above may make use of a library of conditions. The systems and methods described above may be used to stratify a patient with regard to their risk of exacerbation of a disease state. Such stratification may be based on previous data collected from a particular patient or may be based on data for a particular patient population or a patient population as a whole.

While principles of the present disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A method for identifying a disease state of a gastrointestinal tract condition, the method comprising:
   receiving imaging data of a gastrointestinal tract of a patient, wherein the imaging data is obtained from an imaging device;
   receiving gastric activity data of the gastrointestinal tract, wherein the gastric activity data is generated by one or more sensors configured to generate one or more parameters of the gastric activity data;
   processing the imaging data and the gastric activity data to determine a plurality of disease parameter values for a plurality of disease parameters that are indicative of a disease state of a gastrointestinal tract condition;
   evaluating each of the plurality of disease parameters individually based on the plurality of disease parameter values;
   based on the evaluating, determining the disease state is not identifiable based on any one of the plurality of disease parameters alone; and
   in response to the disease state not being identifiable based on any one of the plurality of disease parameters alone:
      determining a disease state value based on at least a subset of the plurality of disease parameter values;
      comparing the disease state value to one or more threshold values, the one or more threshold values indicative of one or more boundaries between a plurality of disease states of the gastrointestinal tract condition; and
      identifying the disease state from the plurality of disease states based on the comparing.

2. The method of claim 1, further comprising at least one of:
   generating and transmitting an alert based on the identified disease state to one or more of the patient, a caregiver of the patient, or medical personnel; or
   determining and causing automatic administration of a treatment to the patient based on the identified disease state.

3. The method of claim 1, wherein the plurality of disease states include at least one of:
   varying severities of the gastrointestinal tract condition;
   statuses of the gastrointestinal tract condition, the statuses including at least active and in remission; or
   indications of a change in disease state over time.

4. The method of claim 1, further comprising:
   receiving one or more previous disease state values determined for the gastrointestinal tract condition; and
   identifying the disease state further based on a comparison of the one or more previous disease state values to the disease state value.

5. The method of claim 1, further comprising:
   receiving additional data associated with the patient, wherein the additional data includes one or more of demographic data, medication, prior medical treatments, mental health information, genomic data, antibody markers, inflammatory markers, histology results, and fecal markers; and
   determining one or more of the plurality of disease parameter values or the disease state value further based on the additional data.

6. The method of claim 1, further comprising:
   weighting one or more of at least the subset of the plurality of disease parameter values prior to determining the disease state value.

7. The method of claim 1, wherein the gastrointestinal tract condition is irritable bowel disease, and the plurality of disease parameters include one or more of lesions, bleeding, stenosis, or vasculature.

8. The method of claim 1, wherein at least one of the plurality of disease parameters includes lesions, and the respective disease parameter value for the lesions is based on at least one of a size and a depth of each of one or more lesions present in the gastrointestinal tract determined based on the imaging data.

9. The method of claim 1, wherein at least one of the plurality of disease parameters includes bleeding, and the respective disease parameter value for the bleeding is based on data associated with one or more of: coagulated blood on a mucosal surface of the gastrointestinal tract, free liquid in a lumen of the gastrointestinal tract, hemorrhagic mucosa of the gastrointestinal tract, or obliteration of blood vessels within the gastrointestinal tract determined from the imaging data.

10. The method of claim 1, wherein at least one of the plurality of disease parameters includes stenosis, and the respective disease parameter value for the stenosis is based on a number of one or more regions of the gastrointestinal tract including narrowing and a degree of the narrowing in each of the one or more regions determined from the imaging data.

11. The method of claim 1, wherein at least one of the plurality of disease parameters includes vasculature, and the respective disease parameter value for the vasculature is based on data associated with one or more of: obliteration, a structure of blood vessels, blood flow, or tissue thickening determined from the imaging data.

12. A method for identifying a disease state of a gastrointestinal tract condition, the method comprising:

receiving imaging data of a gastrointestinal tract of a patient, wherein the imaging data is obtained from an imaging device;

receiving gastric activity data of the gastrointestinal tract, wherein the gastric activity data is generated by one or more sensors configured to generate one or more parameters of the gastric activity data;

processing the imaging data and the gastric activity data to determine a plurality of disease parameter values for a plurality of disease parameters that are indicative of a disease state of a gastrointestinal tract condition;

based on the plurality of disease parameter values, determining the disease state is not identifiable based on any one of the plurality of disease parameters alone; and in response to the determination:
  determining a disease state value based on at least a subset of the plurality of disease parameter values;
  comparing the disease state value to one or more threshold values, the one or more threshold values indicative of one or more boundaries between a plurality of disease states of the gastrointestinal tract condition; and
  identifying the disease state from the plurality of disease states based on the comparing.

13. The method of claim 12, further comprising at least one of:
  based on the identified disease state, generating and transmitting an alert to one or more of the patient, a caregiver of the patient, or medical personnel; or
  based on the identified disease state, determining and causing an administration of a treatment to the patient.

14. The method of claim 12, further comprising:
receiving one or more previous disease state values determined for the gastrointestinal tract condition; and
identifying the disease state further based on a comparison of the one or more previous disease state values to the disease state value.

15. The method of claim 12, further comprising:
receiving one or more additional sets of data; and
determining one or more of the plurality of disease parameter values or the disease state value further based on the one or more additional sets of data.

16. The method of claim 12, wherein the gastrointestinal tract condition is irritable bowel disease, and the plurality of disease parameters include one or more of lesions, bleeding, stenosis, or vasculature.

17. A method for identifying a disease state of a gastrointestinal tract condition, the method comprising:
receiving imaging data of a gastrointestinal tract of a patient, wherein the imaging data is obtained from an imaging device;

receiving gastric activity data of the gastrointestinal tract, wherein the gastric activity data is generated by one or more sensors configured to generate one or more parameters of the gastric activity data;

processing the imaging data and the gastric activity data to determine a plurality of disease parameter values for a plurality of disease parameters indicative of a disease state of a gastrointestinal tract condition;

based on the plurality of disease parameter values, determining whether the disease state is identifiable based on any one of the plurality of disease parameters alone;

when the disease state is determined to be identifiable based on at least one of the plurality of disease parameters, identifying the disease state from a plurality of disease states of the gastrointestinal tract condition based on a comparison of the respective disease parameter value for the at least one of the plurality of disease parameters to one or more first threshold values indicative of one or more boundaries between the plurality of disease states; and when the disease state is determined to not be identifiable based on any one of the plurality of disease parameters alone:
  determining a disease state value based on at least a subset of the plurality of disease parameter values; and
  identifying the disease state from the plurality of disease states based on a comparison of the disease state value to one or more second threshold values indicative of one or more boundaries between the plurality of disease states.

18. The method of claim 17, further comprising at least one of:
  based on the identified disease state, generating and transmitting an alert to one or more of the patient, a caregiver of the patient, or medical personnel; or
  based on the identified disease state, determining and causing an administration of a treatment to the patient.

19. The method of claim 1, wherein evaluating each of the plurality of disease parameters individually based on the plurality of disease parameter values comprises:
  comparing each of the plurality of disease parameter values to corresponding threshold values associated with the plurality of disease parameters for identifying the disease state; and
  determining the disease state is not identifiable based on any one of the plurality of disease parameters alone in response to none of the plurality of disease parameter values meeting or exceeding the corresponding threshold values.

* * * * *